United States Patent [19]

Smith et al.

[11] Patent Number: 5,387,197
[45] Date of Patent: Feb. 7, 1995

[54] TROCAR SAFETY SHIELD LOCKING MECHANISM

[75] Inventors: Richard S. Smith, Loveland; Kevin L. Houser, Centerville; Charles A. Hansford, Hamilton; Pamela K. Jacobs, Loveland; Richard F. Schwemberger, Cincinnati, all of Ohio

[73] Assignee: Ethicon, Inc., Somerville, N.J.

[21] Appl. No.: 21,935

[22] Filed: Feb. 25, 1993

[51] Int. Cl.⁶ .................................. A61M 5/00
[52] U.S. Cl. ........................................ 604/164
[58] Field of Search .................. 604/160–165, 604/766–769, 272–274; 606/184–185, 171; 128/751–754

[56] References Cited

U.S. PATENT DOCUMENTS

| | | | |
|---|---|---|---|
| 3,030,953 | 4/1962 | Koehn | 128/214 |
| 4,020,835 | 5/1977 | Nordstrom et al. | 128/214.4 |
| 4,168,699 | 9/1979 | Hauser | 128/768 |
| 4,177,814 | 12/1979 | Knepshield et al. | 128/348 |
| 4,200,096 | 4/1980 | Charvin | 128/214.4 |
| 4,356,826 | 11/1982 | Kubota | 128/630 |
| 4,535,773 | 8/1985 | Yoon | 604/51 |
| 4,601,710 | 7/1986 | Moll | 604/165 |
| 4,645,491 | 2/1987 | Evans | 604/158 |
| 4,653,475 | 3/1987 | Seike et al. | 128/4 |
| 4,654,030 | 3/1987 | Moll et al. | 604/165 |
| 4,772,267 | 9/1988 | Brown | 604/168 |
| 4,850,973 | 7/1989 | Jordan et al. | 604/157 |
| 4,869,717 | 9/1989 | Adair | 604/51 |
| 4,902,280 | 2/1990 | Lander | 604/165 |
| 4,919,653 | 4/1990 | Martinez et al. | 604/117 |
| 4,931,042 | 6/1990 | Holmes et al. | 604/164 |
| 4,940,458 | 7/1990 | Cohn | 604/51 |
| 4,976,684 | 12/1990 | Broadnax, Jr. | 604/51 |
| 5,030,206 | 7/1991 | Lander | 604/164 |
| 5,066,288 | 11/1991 | Deniega et al. | 604/274 |
| 5,078,700 | 1/1992 | Lambert et al. | 604/264 |
| 5,104,382 | 4/1992 | Brinkerhoff et al. | 604/165 |
| 5,116,353 | 5/1992 | Green | 606/184 |
| 5,127,909 | 7/1992 | Shichman | 604/165 |
| 5,139,485 | 8/1992 | Smith et al. | 604/158 |
| 5,152,754 | 10/1992 | Plylag et al. | 604/164 |
| 5,256,149 | 10/1993 | Banik et al. | 604/164 |
| 5,261,891 | 11/1993 | Brinkerhoff et al. | 604/165 |
| 5,267,965 | 12/1993 | Deniega | 604/164 |

FOREIGN PATENT DOCUMENTS

9304715  3/1992  WIPO .................... 604/165

*Primary Examiner*—C. Fred Rosenbaum
*Assistant Examiner*—Manuel Mendez
*Attorney, Agent, or Firm*—Emil Richard Skula

[57] ABSTRACT

A trocar and trocar obturator assembly having an obturator and a locking mechanism responsive to proximal, axial movement of the trocar obturator is disclosed. The trocar obturator has an elongated obturator shaft having a proximal end and a distal end with a piercing tip mounted thereto. The proximal end of the trocar obturator shaft is slidably mounted in a handle such that the obturator shaft is moveable axially. A protective safety shield having a distal end and a proximal end with a flange member mounted to the proximal end is slidably mounted on the trocar obturator. The safety shield is moveable, axially, between an extended distal position and a retracted proximal position. The protective safety shield is disposed concentrically about the obturator. A lockout arm for locking the safety shield in a locked extended position is mounted in the trocar obturator handle. An actuating collar member is mounted to the proximal end of the obturator shaft in the obturator handle and is moveable with the obturator shaft. The obturator collar disengages the locking arm when moved proximally and engages the locking arm when trocar is armed. The trocar obturator assembly may be concentrically mounted in a trocar cannula having a passageway for receiving the trocar obturator and safety shield. The locking mechanism is actuated by proximal, axial motion of the obturator.

24 Claims, 7 Drawing Sheets

TROCAR SAFETY SHIELD LOCKING MECHANISM

TECHNICAL FIELD

The field of art to which this invention relates is surgical instruments, more particularly, endoscopic surgical instruments.

BACKGROUND ART

The field of endoscopic surgery has become widely embraced by both surgeons and the public. The term "endoscopic" as used herein is defined to include the field of minimally invasive surgery including but not limited to endoscopic, laparoscopic, thoracoscopic and arthroscopic. There are numerous benefits associated with the use of endosurgical techniques including reduced trauma, reduced post-operative recuperation period, reduced incidence of infections, and reduced scarring. In addition, there tends to be a decrease in the length of endoscopic operative procedures when compared with conventional, open procedures, resulting in decreased time under general anesthesia. It is not unusual for patients who have undergone endoscopic surgical operations to be released from the hospital the next day after surgery and to be back on the job within several days. Recuperation periods of 2 to 4 weeks or more are associated with similar operations done using conventional, open surgical procedures.

Numerous endoscopic instruments have been developed which allow the surgeon to perform complex surgical procedures with minimal incisions into the skin and tissue surrounding a particular body cavity. In order to introduce the endoscopic instruments into a body cavity, it is first necessary to puncture and cannulate the body cavity by using a trocar. Trocars are widely known in the art and typically consist of an obturator and a trocar cannula. Trocars may have a protective housing or safety shield around the obturator which covers the sharp piercing tip of the obturator after insertion.

One type of trocar having an obturator safety shield is typically inserted by pressing the distal end of the trocar assembly against the outer skin of the patient with sufficient force to cause the piercing end of the obturator to pierce through the skin, underlying fat, muscle and fascia into a body cavity. Once the surgeon has properly positioned the trocar within the body cavity, the obturator and safety shield are removed, and, the trocar cannula is then available as a pathway, e.g., for the insertion of conventional endoscopic instruments and devices.

Conventional trocar obturators typically consist of an elongated obturator shaft having a distal piercing tip. The proximal end of the obturator shaft is typically mounted in an obturator handle. A biased safety shield for covering the piercing tip may be concentrically mounted about the obturator such that the shield is slidable between a fully extended position, wherein the piercing tip is covered, and a fully retracted position, wherein the piercing tip is exposed. The trocar obturator is, typically, concentrically mounted within a trocar cannula to form a trocar.

Conventional trocar cannulas typically consist of a distal cannula tube and a proximal cannula handle. The cannula tube is typically inserted into a patient (along with a section of the obturator shaft), while the proximal handle of the trocar cannula typically remains outside of the patient. Trocar cannula handles typically contain a spring-loaded flapper-type valve which seals the proximal opening of the trocar cannula, thereby allowing the patient's body cavity to remain insufflated with a gas by preventing the gas from escaping through the trocar cannula after the trocar obturator has been removed. The trocar cannula handle typically has an exterior control lever to manually control the position of the flapper valve and to indicate the position of the flapper valve.

Most surgeons prefer using a trocar having a protective sleeve or safety shield concentrically mounted about the trocar obturator. The safety shield is designed to help prevent the piercing tip of the trocar obturator from inadvertently piercing or cutting internal organs or blood vessels or tissue after penetration has been made through the layers tissue surrounding a body cavity. The safety shield typically operates in the following manner. When the distal end of the trocar is placed against the outer skin surrounding a patient's body cavity, the tip of the trocar obturator and the tip of the safety shield are typically in contact with the skin. As the surgeon pushes the trocar obturator into the layers of tissue and fascia surrounding the body, the concentrically mounted safety shield is displaced axially, against a biasing force, in a proximal direction to a retracted position, thereby exposing the piercing point of the obturator and allowing the tip to cut through tissue. The biasing force is typically provided by a spring member such as a compression spring. After the piercing tip has penetrated into the body cavity, the distal biasing force on the safety shield causes the safety shield to move rapidly in a distal direction to an extended position, thereby covering the piercing point of the obturator and preventing the obturator from piercing or cutting any internal tissue, organs, or blood vessels. Typically, the trocar assembly will have a locking mechanism which engages the safety shield and prevents the safety shield from displacing and uncovering the piercing tip of the obturator after the obturator has passed into the body cavity.

Although locking mechanisms for safety shields in trocar obturators are known in this art, there is a constant need in this art for advancement and progress with regard to the design of endoscopic surgical instruments, in particular with regard to the design of trocars and safety shield locking mechanisms for trocars.

Therefore, it is an object of this invention to provide a trocar having a safety shield and a lockout mechanism wherein the safety shield lockout mechanism is triggered by axial, proximal movement of the trocar obturator.

It is a further object of the present invention to have a locking mechanism for a safety shield of a trocar obturator which is reliable.

DISCLOSURE OF THE INVENTION

Accordingly, a trocar obturator assembly is disclosed. The trocar obturator assembly has an elongated obturator shaft having a proximal end and a distal end. The distal end of the trocar obturator shaft has a piercing tip mounted thereto. The proximal end of the trocar obturator shaft is slidably mounted in a trocar obturator handle such that the obturator shaft is moveable, axially, both distally and proximally and is biased distally by biasing means mounted in the handle. A protective safety shield, having a distal end and a proximal end, is slidably mounted on the trocar obturator. The safety shield is moveable, axially, between an extended position and a retracted position. The protective safety shield is disposed concentrically about the obturator. Mounted in the obturator handle are distal biasing means, such as a compression spring, acting on the proximal end of the safety shield to move the shield to an extended position to cover the piercing tip. Also mounted in the handle is a safety shield locking means for locking the safety shield in an extended position. The safety shield locking means is actuated by actuating means. The locking means may be a lockout arm mounted in the handle, the lockout arm having a proximal fixed end and a distal free end such that the free end engages the safety shield to retain the safety shield in a locked position. The lockout arm preferably has a clearance hole. The actuating means is responsive to proximal, axial movement of the obturator shaft resulting from pressure or force upon the obturator piercing tip. The actuating means preferably comprises an obturator collar member, having an engagement arm, mounted to the proximal end of the obturator shaft in the obturator handle and moveable with the obturator shaft. The obturator collar engages the lockout arm when the trocar obturator is armed and prevents the lockout arm from engaging the safety shield, thereby allowing the safety shield to slide proximally in an axial manner. The obturator collar member actuates the locking means when the engagement arm slides into the clearance hole of the lockout arm as the obturator shaft moves proximally, thereby allowing the lockout arm to re-engage the safety shield. Optional reset means are mounted in the handle for re-arming the trocar obturator assembly by disengaging the lockout arm from the safety shield.

Another aspect of the present invention is a trocar having a trocar obturator assembly and a trocar cannula. The trocar obturator assembly has an elongated obturator shaft having a proximal end and a distal end. The distal end of the trocar obturator shaft has a piercing tip mounted thereto. The proximal end of the trocar obturator shaft is slidably mounted in a trocar obturator handle such that the obturator shaft is moveable, axially, both distally and proximally and is biased distally by biasing means, such as a compression spring, mounted in the handle. A protective safety shield, having a distal end and a proximal end, is slidably mounted on the trocar obturator. The safety shield is moveable, axially, between an extended position and a retracted position. The protective safety shield is disposed concentrically about the obturator. Mounted in the obturator handle are distal biasing means acting on the proximal end of the safety shield to move the shield to an extended position to cover the piercing tip. Also mounted in the handle is a safety shield locking means for locking the safety shield in an extended position. The safety shield locking means is actuated by actuating means. The locking means may be a lockout arm mounted in the handle, the lockout arm having a proximal fixed end and a distal free end such that the free end engages the safety shield to retain the safety shield in a locked position. The lockout arm preferably has a clearance hole. The actuating means is responsive to proximal, axial movement of the obturator shaft resulting from pressure or force upon the obturator piercing tip. The actuating means preferably comprises an obturator collar member, having an engagement arm, mounted to the proximal end of the obturator shaft in the obturator handle and moveable with the obturator shaft. The obturator collar engages the lockout arm when the trocar obturator is armed and prevents the lockout arm from engaging the safety shield, thereby allowing the safety shield to slide proximally in an axial manner. The obturator collar member actuates the locking means when the engagement arm slides into the clearance hole of the lockout arm as the obturator shaft displaces proximally, thereby allowing the lockout arm to re-engage the safety shield. Optional reset means are mounted in the handle for re-arming the trocar obturator assembly by disengaging the lockout arm from the safety shield. The trocar obturator assembly is concentrically mounted in a trocar cannula having an interior passage therethrough for receiving the trocar obturator and safety shield. The trocar cannula has an elongated trocar cannula tube which is mounted in a trocar cannula handle.

Yet another aspect of the present invention is a method of performing an endoscopic surgical procedure using the above-described trocar having the above-described trocar locking mechanism.

Still yet another aspect of the present invention is a trocar cannula having an elongated cannula tube mounted in a handle. The distal tip of the cannula tube is both chamfered and tapered.

Yet another aspect of the present invention is a slidable button for arming a safety shield locking mechanism. This button also indicates the status of the locking mechanism, indicating if the instrument is in the armed or locked state.

Other features and advantages of the invention will become more apparent from the following description and accompanying drawings.

BEST MODE FOR CARRYING OUT THE INVENTION

Figure 1:
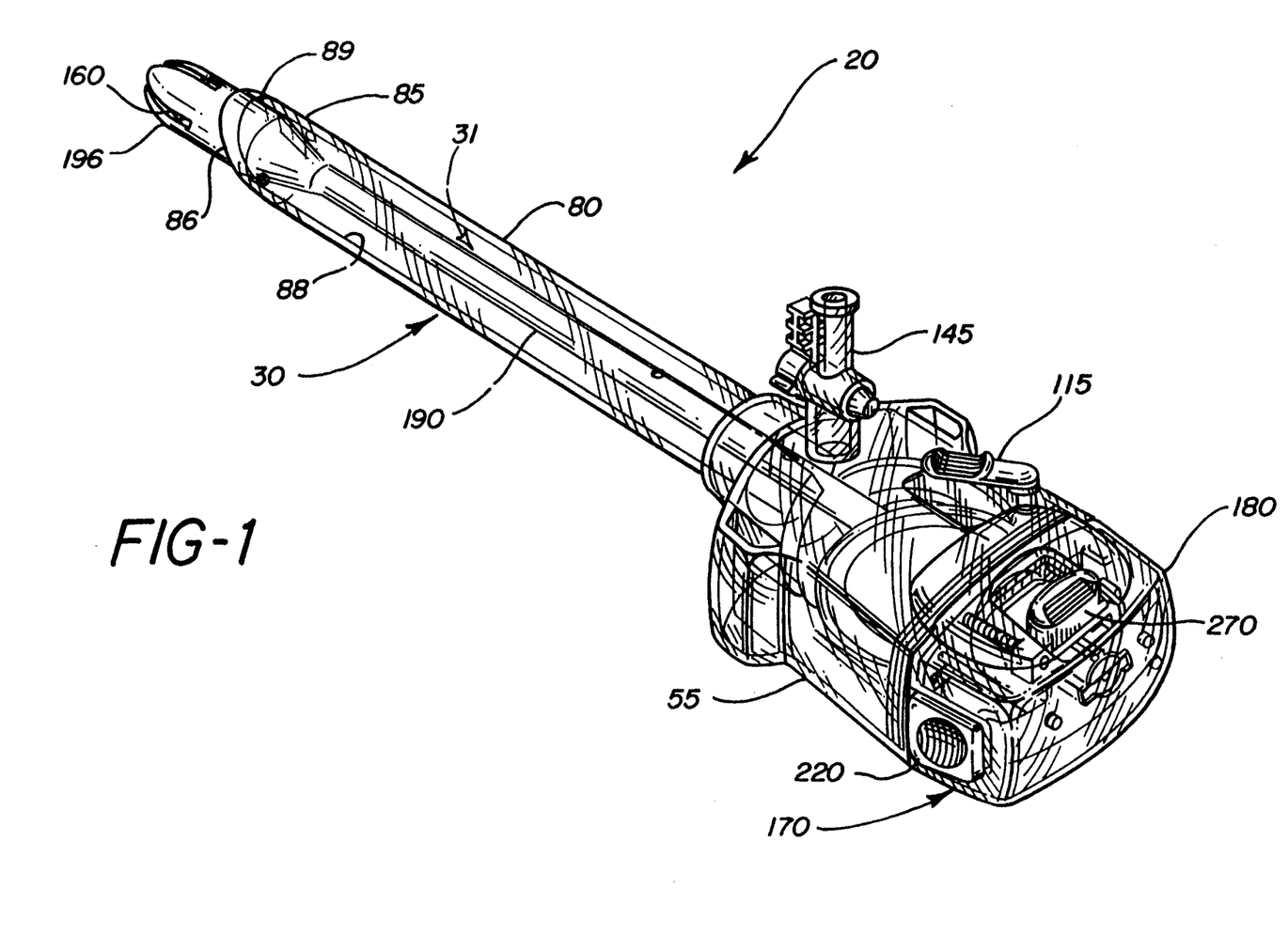
FIG. 1 is a perspective view of an embodiment of a trocar of the present invention having a safety shield locking mechanism of the present invention.
Figure 2:
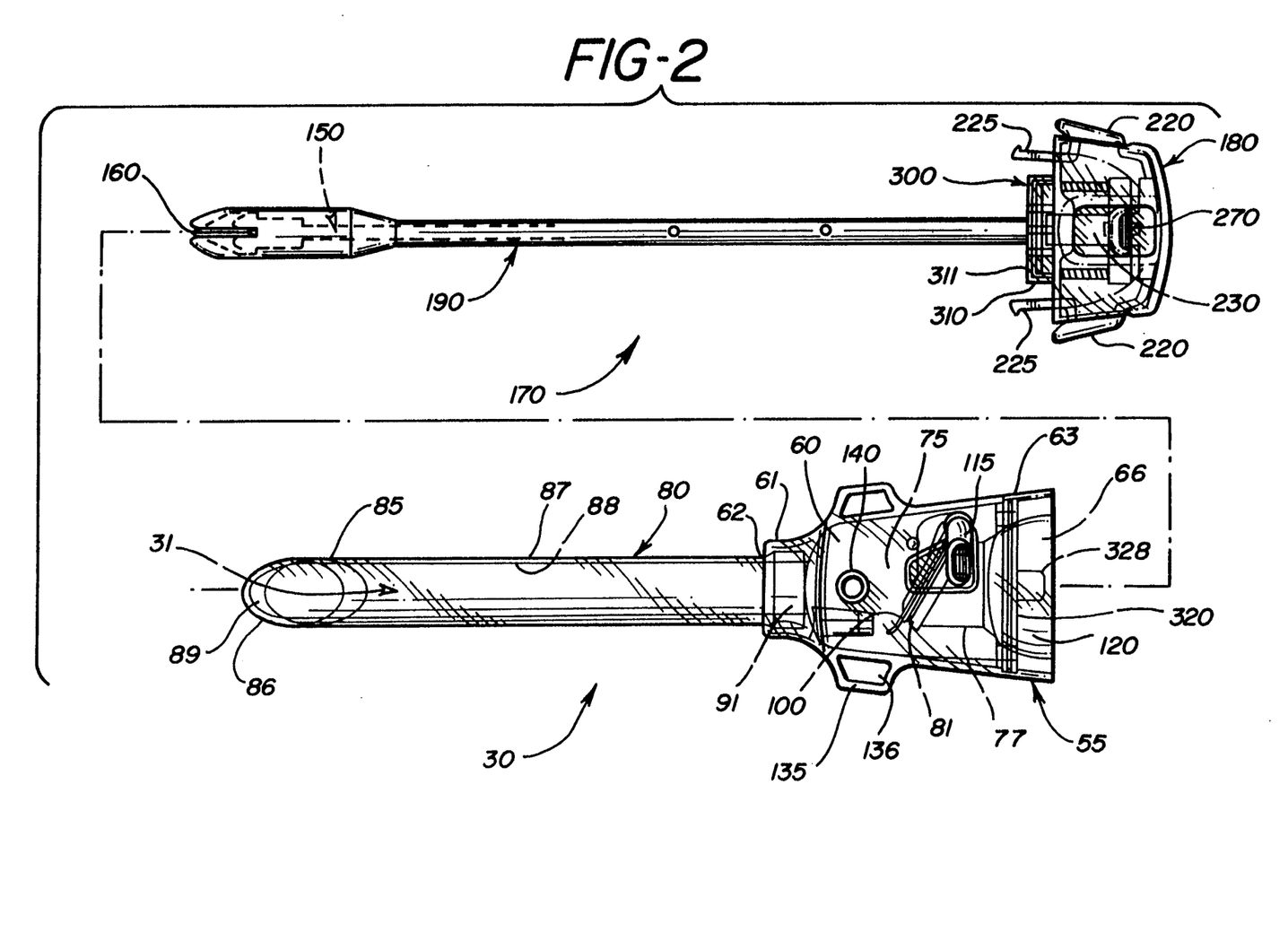
FIG. 2 is a plan view of a trocar obturator and a trocar cannula of the present invention.

The trocar 20 of the present invention is illustrated in FIGS. 1 and 2. It can be seen that the trocar 20 has trocar cannula 30 and trocar obturator assembly 170.

Figure 3:
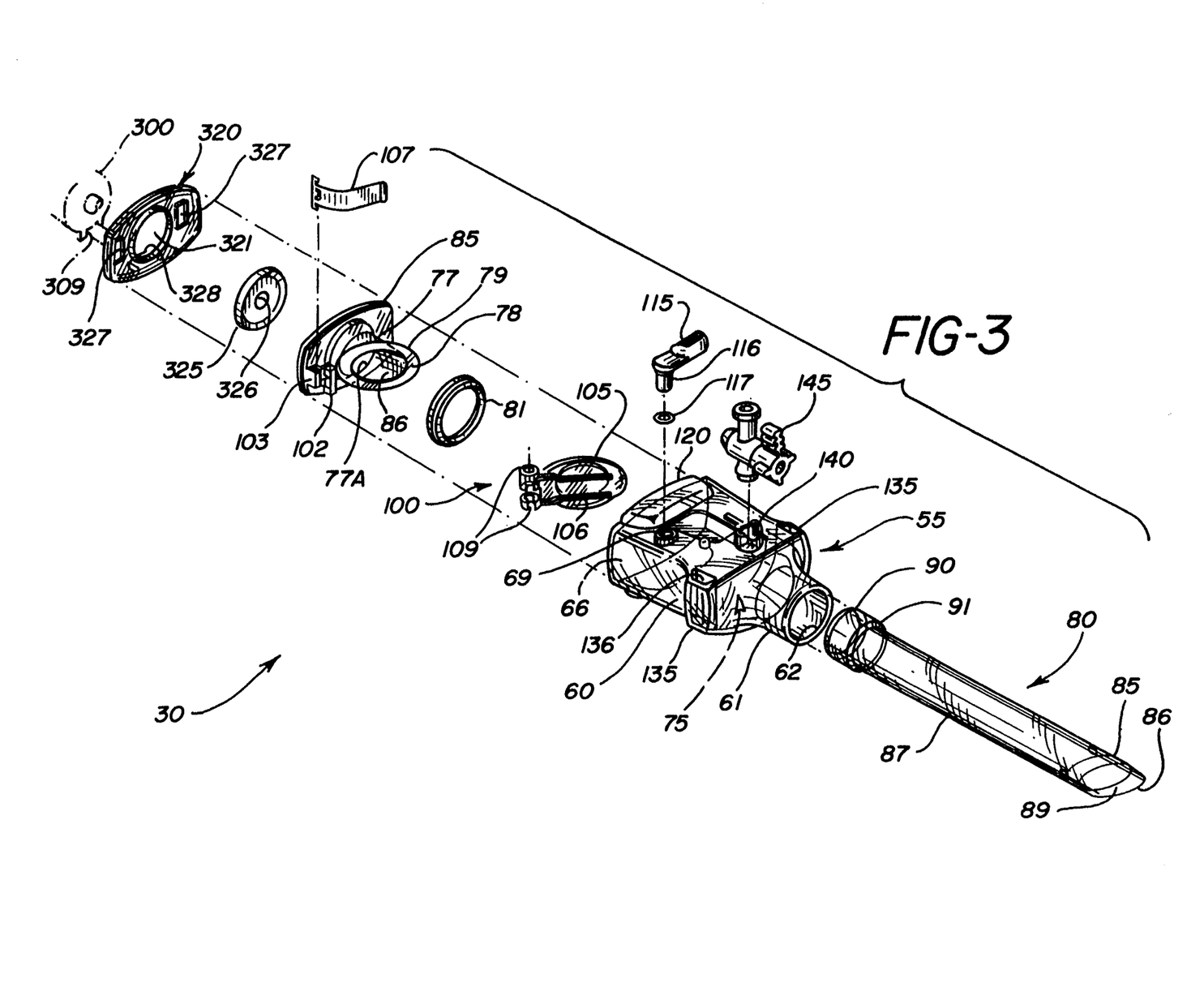
FIG. 3 is an exploded perspective view of a trocar cannula of the present invention.
Figures 6, 6A:
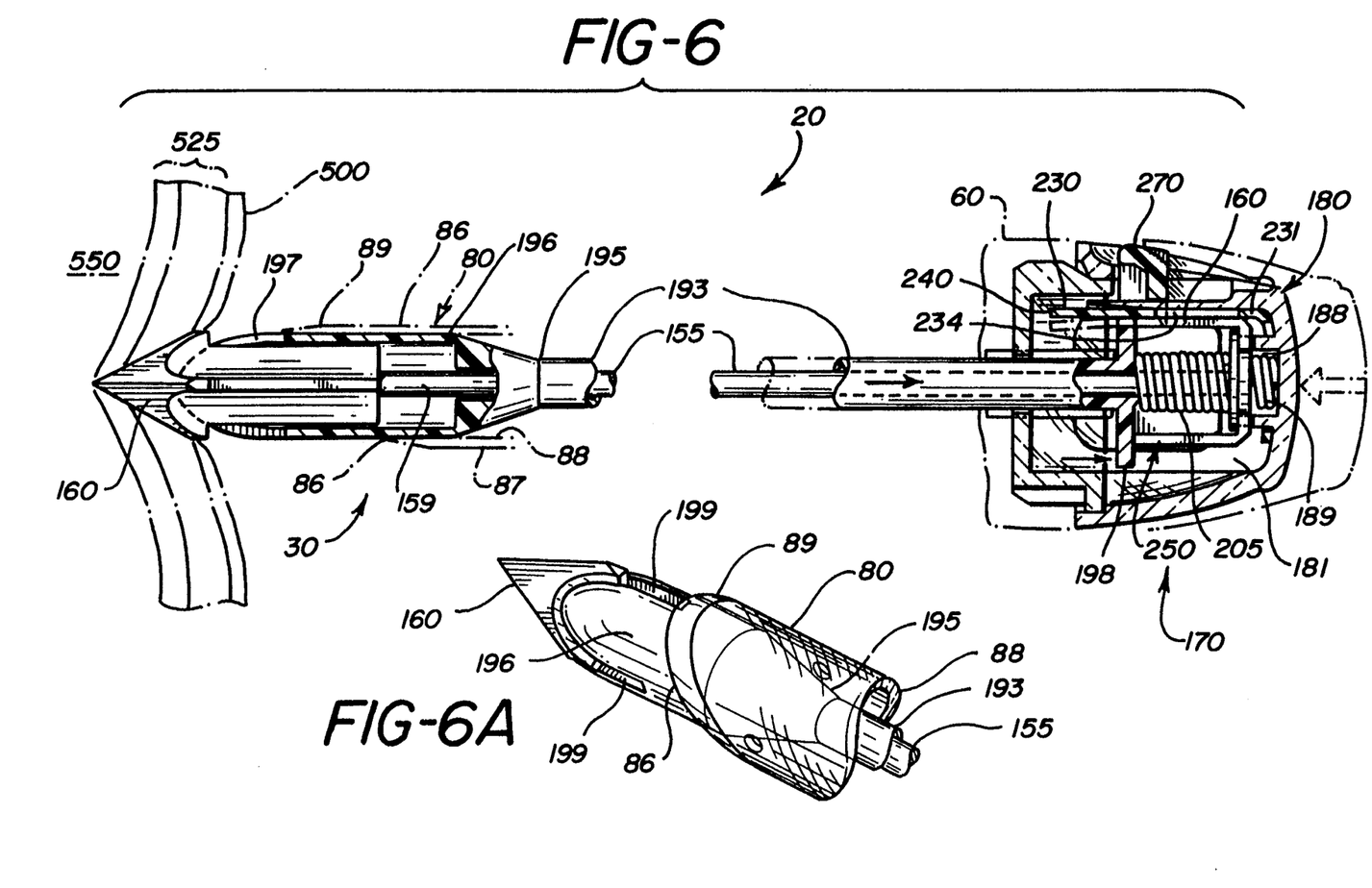
FIG. 6 is a side view of the trocar of the present invention during insertion into a body cavity with the safety shield retracted, the obturator shaft displaced proximally and the tip of the obturator exposed; the cannula handle and the proximal end of the safety shield are partially cut away.
FIG. 6A is a partial perspective view of the distal end of the trocar of FIG. 6 illustrating the tip of the obturator exposed with the safety shield in a retracted position; the distal end of the cannula is also illustrated.

Referring to FIGS. 1, 2, and 3, trocar cannula 30 is seen to have trocar cannula tube 80 and trocar cannula handle 55. Trocar cannula 30 has passageway 31 therethrough for receiving various members such as trocar obturators, conventional endosurgical instruments and the like. Trocar cannula tube 80 is an elongate tube having open distal end 85 and open proximal end 90. Referring also to FIG. 6A, the tip 86 of distal end 85 is seen to be angulated or beveled with respect to the longitudinal axis of cannula tube 80. The tip 86 is also seen to have a tapered or chamfered section 89 wherein the outer wall 87 of tube 80 tapers or bevels inwardly toward inner wall 88 of tube 80. The angle of the bevel and the degree or inclination of the chamfer are sufficient to effectively reduce the force to penetrate of a trocar 20. It is believed that the combination of the chamfer and taper of the end 86 helps reduce the force to penetrate. The bevel angle with respect to the longitudinal axis of tube 80 will typically be about 15° to about 60°, and in the present embodiment preferably about 45°. The angle of the chamfer with respect to the longitudinal axis of tube 80 will typically be about 5° to about 45°, more typically about 5° to about 15°, and in the present embodiment preferably about 6°.

Proximal end 90 is seen to have shoulder 91 for mounting in trocar cannula handle 55,. Trocar cannula handle 55 has hollow housing 60. Housing 60 has distal aperture 62 for receiving proximal end 90 and shoulder 91 of trocar cannula tube 80. Annular member 61 projects distally from the distal end of housing 60 about distal aperture 62. Housing 60 also has proximal aperture 66.

Cavity 75 within housing 60 contains tubular member 77 which extends from proximal aperture 66 into the cavity 75 in a distal direction along the longitudinal axis of the trocar cannula 30. Tubular member 77 has an interior passageway therethrough. Cavity 75 is in communication with interior passageways of both tube 80 and tubular member 77. The distal end 79 of tubular member 77 is seen to be angulated. Flange 78 is seen to extend radially from the distal end of tubular member 77. The proximal end of tubular member 77 is mounted to mounting plate 85. Mounting plate 85 contains central distal aperture 86. Pin member 102 is seen to extend from the distal side of plate member 85. Spring retaining member 103 is seen to project distally next to pin member 102. A sealing ring 81 mounted about flange 78 at distal end 79 of tubular member 77 forms a valve seat which contacts the face 105 of flapper valve 100.

The flapper valve 100 is seen to be a plate-like member. Extending from the flapper valve 100 are a pair of opposed mounting yoke members 109. The flapper valve 100 is seen to have proximal side 105 and distal side 106. Flapper valve 100 is mounted on pin member 102 via mounting yoke members 109 and biased rearward against sealing ring 81 by spring member 107 in order to provide a gas-tight seal. Spring member 107 is seen to be a curved leaf spring. One end of spring member 107 is mounted to the interior distal face of plate 85 between spring retaining member 103 and pin member 102. The other end of the spring member 107 engages the distal side 106 of the flapper valve 100. Pivotally mounted lever 115, which is mounted to one of the yoke members 109, indicates the position of flapper valve 100 between a closed position, wherein sealing ring 81 sealingly engages flapper valve proximal face 105, and a fully open position. Lever 115 is seen to have pivot pin 116 which is mounted through o-ring 117, through aperture 69 in frame 60, and into a yoke member 109, so that pivoting flapper valve 100 will cause lever 115 to pivot, and conversely, pivoting lever 115 will cause valve 100 to pivot between open and closed positions.

The proximal end of housing 60 has external proximal cavity 120. Proximal wall 63 of housing 60 is located in cavity 120 and consists in part of proximal elate member 320 which is mounted in cavity 120. Located in the center of proximal plate member 320 is the aperture 321. Ring gasket 325 is seen to be mounted between the distal side of proximal plate member 320 and the proximal side of mounting plate 85. Mounting plate 85 and proximal plate member 320 form proximal wall 63 of handle frame 60 having proximal aperture 66. Ring gasket 325 is a resilient disk-like member having a central hole 326 which is expandable to engage the surfaces of any instruments inserted therethrough so as to provide a gas-tight seal. Gasket 325 is made from a suitable, conventional polymeric material having sufficient elasticity to effectively allow deformation of the gasket 325 about the surfaces of an instrument or other device inserted therethrough. Cavities 327 are disposed to either side of aperture 321 in proximal plate member 320. Cavities 327 form part of a locking mechanism for locking together the trocar obturator assembly 170 and the trocar cannula 30 to form the trocar 20, as will be further described in more detail below. The bosses 309 of end cap 300 are received in cavity 120 of frame 60. Extending from the bottom center of plate member 320 is at least one tab member 328 which engages the bottom bosses 309 of end cap 300.

As can be seen in FIG. 1, FIG. 2 and FIG. 3, frame 60 of trocar cannula handle 55 projects outwardly on both sides toward the distal end of frame 60 to form finger grips 135. Holes 136 are seen to extend through each grip 135. Between finger grips 135, tubular section 140 is seen to extend upwardly from the top of frame 60 to form a channel in communication with cavity 75. Valve 145 is mounted to tubular section 140. Valve 145 may be any type of conventional valve, including a check valve, although it is preferred to use a plug valve. However, it should be noted that check valves do not typically communicate with insufflators. Valve 145 may be used, for example, as a means to insufflate and desufflate.

Figures 4, 4A:
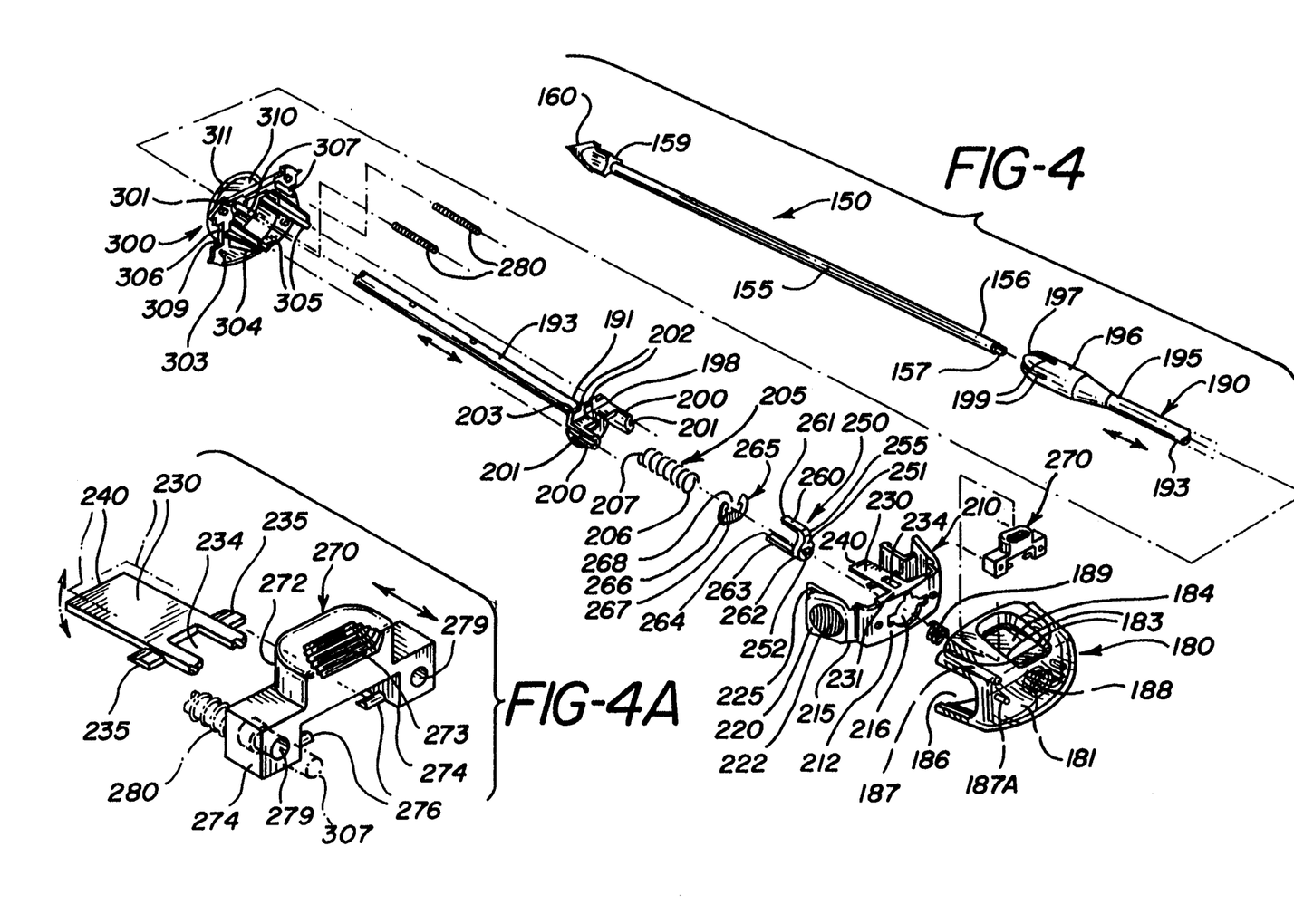
FIG. 4 is an exploded perspective view of a trocar obturator assembly of the present invention illustrating the safety shield locking mechanism components.
FIG. 4A is a partial exploded perspective view illustrating the arming button and the lockout arm.

Referring to FIG. 1, FIG. 2 and FIG. 4, as well as FIGS. 5–8, trocar obturator assembly 170 is seen to comprise obturator 150 and handle 180. Obturator 150 is seen to have an elongated obturator shaft 155 having a distal piercing tip 160. The obturator shaft 155 has distal end 159 and proximal end 156. The piercing tip 160 of obturator 150 may be any type of trocar obturator piercing tip which is effective to pierce tissue such as those disclosed in U.S. Pat. No. 5,066,288 and U.S. Pat. No. 5,114,407 which are incorporated by reference. In an alternate embodiment (not shown), the tip 160 consists of a razor blade mounted in mounting grooves contained in the distal end 159 of shaft 155.

The proximal end 156 of the obturator shaft 155 is slidably mounted in handle 180 with the tip 157 of the proximal end 156 of shaft 155 being displaceable into cavity 188 contained in the interior, proximal wall of trocar obturator handle 180. The trocar obturator 150 has a range of proximal motion, or stroke, with respect to the handle 180 sufficient to effectively actuate the safety shield locking mechanism. Although the stroke may vary according to the size of the trocar, it is preferred that the stroke be invariant and independent of the size of the trocar. For example, the stroke for an obturator will be sufficient to effectively actuate the locking mechanism, and preferably will be about 0.060 inches plus and minus about 0.015 inches.

Trocar obturator handle 180 is a hollow member containing interior cavity 181. The handle 180 is seen to have top slots 183 on either side of plate member 184, and a pair of opposed lateral openings 186. Plate member 184 is a cantilevered member extending distally from the proximal end of handle 180. Extending axially and distally from the proximal interior wall of handle 180 are the cap mounting posts 187 and the latch member mounting posts 187A. The distal end of handle 180 is open and receives mounting cap 300. As mentioned previously, cavity 188 is contained in the interior proximal wall of handle 180 for receiving the proximal tip 157 of the obturator shaft 150. Mounted in the cavity 188 is the compression spring 189. Compression spring 189 abuts the collar 251 and biases the shaft 150 distally. Optionally, the shaft 150 may be biased by cantilevered spring members extending from either side of the bore 216 of latch member 210 which provide a distal bias against the proximal tip 157 of obturator shaft 150 or collar 251.

Safety shield 190 is an elongated, tubular member slidably mounted, axially, on obturator shaft 155. The shield 190 is seen to be concentrically disposed about obturator shaft 155. The shield 190 has tube member 193. Safety shield 190 is seen to have proximal end 191 and distal end 195. Safety shield 190 also has radial outwardly extending end flange 198 mounted to the proximal end 191 of tube member 193. Flange 198 is seen to have proximally extending fin members 200 having slots 201 to provide stability when safety shield 190 is sliding. The proximal end 191 of safety shield 190 is slidably mounted, axially, and contained within cavity 181 of handle 180. The distal end 195 of the safety shield 190 is seen to have tip 196. It is particularly preferred that tip 196 have a rounded bullet shape or profile, however tip 196 may have any profile conventionally used for safety shields. Tip 196 has opening 197 and slots 199 for piercing tip 160 to extend through. Opening 197 and slots 199 are shaped to accommodate the particular configuration of the piercing tip 160 which is used for obturator 150. Flange 198 is seen to have optional upwardly extending teeth 202 extending from flat section 203. Lockout arm 230 engages teeth 202 if present on flange 198, otherwise lockout arm 230 engages the body of flange 198. A compression spring 205 is concentrically mounted about the proximal end 156 of obturator shaft 155 in cavity 181. The proximal end 206 of spring 205 abuts against the retaining ring 265 while the distal end 207 abuts against the proximal face of flange 198 of safety shield 190. Compression spring 205 provides a distal biasing force against flange 198 of slidably mounted safety shield 190 so that safety shield 190 is moveable, axially, between a fully extended position, wherein the piercing tip 160 of obturator 150 is covered, and a fully retracted position, wherein piercing tip 160 is exposed.

As previously mentioned, in a particularly preferred embodiment, safety shield 190 will have a bullet shaped nose 196 at the distal end. The bullet shaped nose 196 may be made from clear materials or opaque materials. It is particularly preferred to manufacture nose 196 from black, opaque materials. The safety shield 190 will preferably be assembled by mounting the distal end 195, having tip 196, to the tubular member 193 using conventional mounting techniques such as bonding, snapping or welding. Similarly the flange 198 may be mounted to the proximal end 191 of the tubular member 193 However, the shield 190 may be manufactured in a single piece, for example, by conventional molding techniques. It is also preferred that tube member 193 be made from an opaque material.

Latch member 210 is seen to have mounting beam member 212. Extending axially from the outer ends of member 212 are the latches 220. Each latch 220 is connected to beam member 212 by living hinge-type or cantilever connections 215. Beam member 212 is seen to have central bore 216 extending therethrough. Optionally, there may be present spring members extending radially inward from the bore 216. The optional spring members exert a distal bias on the proximal tip 157 of the obturator shaft 155 in place of or in addition to spring 189. Each latch 220 is seen to have finger pad 222 and axially extending tab member 225. The finger pads 222 extend through openings 186 of handle 180. The latches 220 allow the trocar obturator assembly 170 to mate with and be locked into trocar cannula 30.

As can be seen in FIGS. 4, 4A, 5, 6, and 8, extending distally from the top of the center of beam member 212 is a lock-out arm 230. Lockout arm 230 is an elongate, rectangularly shaped beam member having fixed proximal end 231 and free distal end 240. Located toward the proximal end 231 of lockout arm 230 is the knife collar clearance hole 234. Extending outwardly from the lockout arm 230 are a pair of opposed reset tabs 235. The knife collar arm 260 is contained within collar clearance hole 234 when the safety shield locking mechanism is engaged. Tab members 235 are engaged by tab members 276 of reset button 270 to rearm the trocar obturator assembly 170.

Concentrically mounted to the proximal end 156 of the trocar obturator shaft 155 is the knife collar 250. The knife collar 250 is made up of an annular member 251 with a circular hole 252 extending therethrough. Extending radially from the periphery of knife collar 250 is the member 255. Extending axially and distally from the member 255 is the knife collar arm 260 having free distal end 261. The knife collar 250 is seen to have a second, optional knife collar arm 263 which extends axially and distally from a second radially extending member 262. The free distal end 264 of the second, optional arm 263 may engage the flange 198 of the safety shield 190.

The retaining ring 265 is a c-shaped, disk-like member having a central, irregular hole 266 extending therethrough. The ring 265 is seen to have flat section 267 and opening 268. The ring 265 is concentrically mounted to obturator shaft 155 between knife collar 250 and spring 205 in a mounting groove on the obturator shaft 155.

The reset button 270 is slidably mounted in the top slots 183 of handle 180 on plate member 184. The reset button 270 rides on plate member 184. The reset button 270 has upwardly extending top section 272 and downwardly extending legs 274. Extending inwardly from each leg 274 is a tab member 276. The tab members 276 slidably engage the tabs 235 on lockout arm 230. The top 272 of button 270 has grooves 273 to enhance gripability. Each leg 274 of reset button 270 has axially extending cylindrical cavities 279 extending from distal face of each leg 274 and continuing proximally through the legs. The cavities 279 receive the reset springs 280 and the mounting pins 307.

The lockout arm 230 has a free state in which it engages the safety shield 190. Moving the reset button 270 distally, causes the tab members 276 to engage the back side of the lockout arm reset tabs 235 and cam the lockout arm forward. This allows the knife collar 250 to move distally and hold the lockout arm 230 in the armed position (safety shield 190 is free to move proximally). Releasing the reset button 270, allows the members 276 of the reset button 270 to rest against the tabs 235 of the lockout arm 230. The reset button 270 is held in its distal position, indicating that the trocar 20 is armed and ready for use. As the trocar 20 is actuated, the knife collar 250 moves proximally into the clearance hole 234 in the lockout arm 230 allowing the lockout arm 230 to return to its free state. Movement of the lockout arm 230 to its free state, releases the reset button 270 and allows the reset button 270 to return to its proximal position. As the tab members 276 pass on the front side of the reset tabs 235, the tab members 276 cam the lockout arm 230 back. After the tab members 276 have passed the tabs 235, the lockout arm 230 returns to its free state. In this position, the lockout arm 230 is ready to be rearmed.

If the reset button 276 is held distally during insertion of the trocar 20, the lockout arm 230 returns to its free state and engages the safety shield 190. The reset button 270 will return to its distal position when released in the manner described in the previous paragraph.

The end cap 300 is seen to be a substantially rectangularly shaped flat plate-like member which mates with the handle 180 to enclose the distal end of handle 180. Central hole 301 extends through end cap 300. The end cap 300 is seen to have proximally extending members 304 having rails 305 for guiding and retaining safety shield 190. Rails 305 are engaged by slots 201 of fin members 200. Above each member 304 are the reset spring mounting pins 307. Each reset spring 280 is mounted onto a mounting pin 307. The end cap 300 has a pair of opposed rectangularly shaped openings 309 for receiving the tab members 225. The mounting holes 303 are contained in and extend through the corners of end cap 300 for receiving the mounting posts 187. Extending distally from the center of the end cap 300 is the cylindrical member 310 having end face 311. Central hole 301 extends through end face 311. Also extending from the bottom and top of the end cap 300 are the central raised bosses 309. Bosses 309 serve as alignment pins to align the trocar obturator 170 with the trocar cannula 30. Bosses 309 are inserted into cavity 120 of frame 60. The bottom bosses 309 engage tab member 328 which extends from the bottom of plate member 320, thereby allowing the obturator assembly 170 to be inserted and locked into cannula 30 only with the top up.

The trocar obturator assembly 170 is assembled in the following manner. First, an obturator sub-assembly is made as follows. Initially, the tubular member 193 of the safety shield 190 is fed through the central hole 301 in the end cap 300. Next, the distal end 195 having bullet tip 196 is snapped onto or bonded to the distal end of tubular member 193 (having a flange 198 molded, preferably, to the proximal end 191) to form safety shield 190. Next, the obturator 150 is inserted into the safety shield 190. Then spring 205 is concentrically mounted onto the distal end 156 of the obturator shaft 155. Then the washer 265 is mounted onto the obturator shaft 155. The knife collar 250 is then attached to the proximal end 156 of the obturator shaft 155 using conventional attachment methods including adhesives, fasteners, welding, brazing, press fits and the like. The knife collar 250 may, if desired, be slidably mounted onto the shaft 155. The latch member 210 is then mounted to the mounting posts 187A in handle 180 and secured by conventional methods such as ultrasonic welding, conventional adhesives and the like. Next, the legs of reset button 270 are placed into slots 183 in the handle 180 and is mounted such that it slidably engages the lockout arm 230. The knife spring 189 is dropped into the cavity 188 in handle 180. Then, the reset springs 280 are placed onto the pins 307. Then, the obturator sub-assembly is placed into the cavity 181 of handle 180 with tip knife collar 250 in engagement with spring 189, and with knife collar arm 260 in engagement with lockout arm 230. Finally, the end cap 300 is mounted onto the distal end of the handle 180 by placing cap 300 onto the mounting posts 187 such that mounting posts 187 extend through holes 303 and the pins 307 and springs 280 are inserted into cavities 279 in the reset button 270. The cap 300 is secured by conventional methods such as those previously mentioned.

The trocar 20 is assembled for use by concentrically mounting the obturator assembly 170 in the trocar cannula 30. This is accomplished by inserting the distal end 159 of obturator 150 (i.e., the bullet shaped tip 196 and the piercing tip 160) into aperture 66 of housing 60 through gasket ring 325 and into tubular member 77. Gasket ring 325 is sufficiently sized and designed to effectively sealingly engage safety shield 190 (and other various endoscopic instruments inserted into cannula 30) by displacing radially outwardly and axially. As the tip 196 of the safety shield 190 contacts the proximal face 105 of flapper valve 100, it causes flapper valve 100 to pivot distally about pin member 102 to an open position, as seen in FIG. 1. The obturator shaft 155 and the safety shield 190 are then slid through the cavity 75, into and through the aperture 62 and into trocar cannula tube 80. A sufficient axial force applied in a distal manner against the handle 180 of trocar obturator assembly 170 causes the tab members 225 and the latches 220 to be displaced inwardly. As the trocar obturator assembly 170 is moved further axially within the trocar cannula 30, tab members 225 are displaced into cavities 327 contained in the wall 63 of housing 60 in cavity 120 and biased outward by hinges 215, thereby locking the trocar obturator assembly 170 to the trocar cannula 30.

The trocar 20 operates in the following manner. The trocar 20 is armed by displacing the reset button 270 distally. Displacing reset button 270 distally causes the tab members 276 to engage the back side of the reset tabs 235 and cam the lockout arm 230 forward causing the tab members 276 to engage the back side of the lockout arm reset tabs 235 and cam the lockout 230 arm forward. This allows the knife collar 250 to move distally and hold the lockout arm 230 in the armed position (safety shield 190 is free to move proximally). Releasing the reset button 270, allows the members 276 of the reset button 270 to rest against the tabs 235 of the lockout arm 230. The reset button 270 is held in its distal position, indicating that the trocar 20 is armed and ready for use. As the trocar 20 is actuated, the safety shield 190 is free to slide proximally. The trocar 20 of the present invention in the armed mode is seen in FIG. 5.

Figure 5:
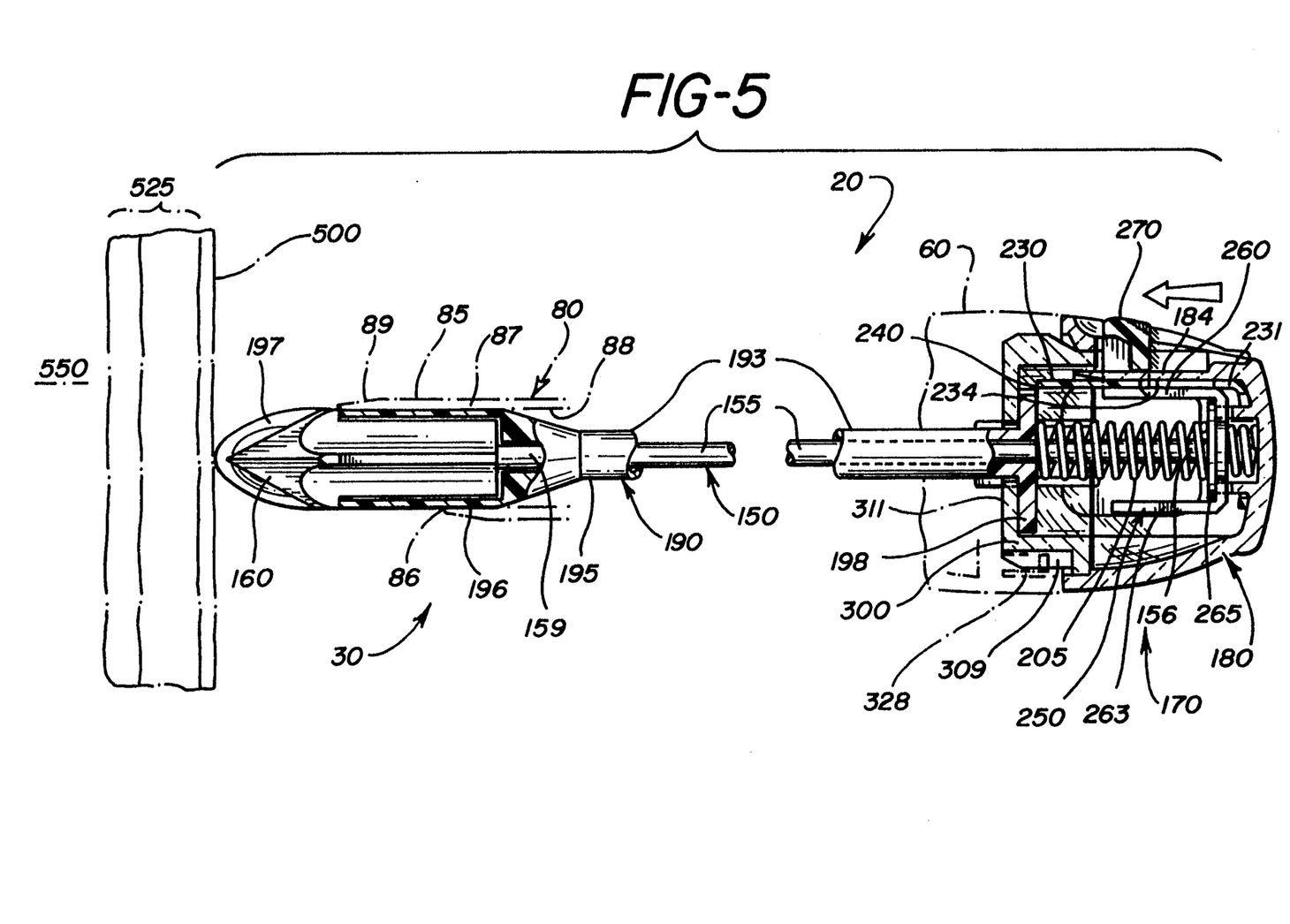
FIG. 5 is a partial, cross-sectional side view of the trocar of the present invention shown in an armed mode immediately prior to insertion into a body cavity; the cannula handle and the proximal end of the safety shield are partially cut away.
Figures 7, 8:
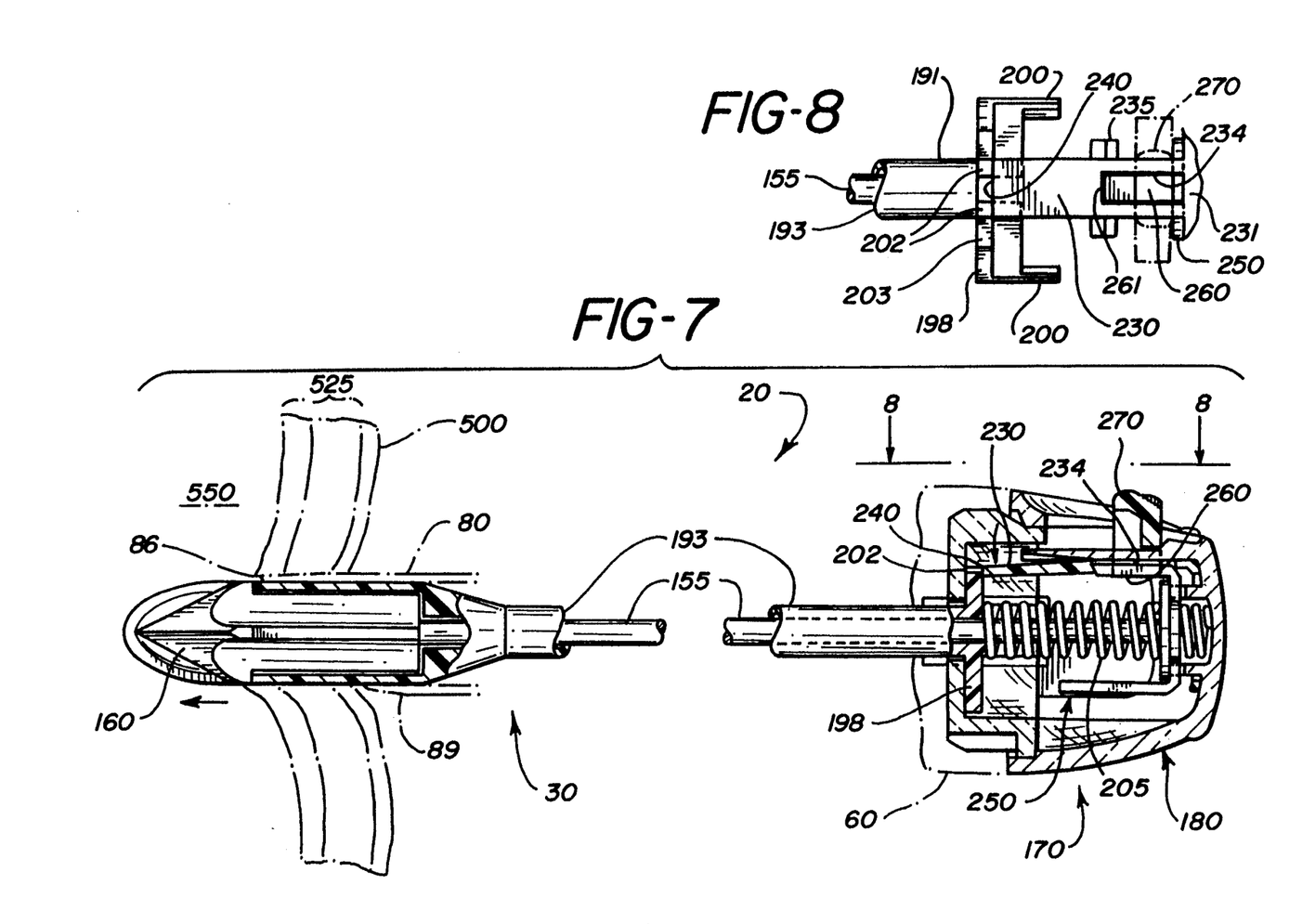
FIG. 7 is a side view of the trocar of the present invention in an armed mode immediately after insertion into a body cavity with the safety shield in a locked, extended position covering the tip of the obturator; the cannula handle and the proximal end of the safety shield are partially cut away.
FIG. 8 is a partial cross-sectional top view of the obturator handle of FIG. 7 along View Line 8—8 illustrating the lockout arm engaging the safety shield flange in a locked-out configuration.

Referring to FIGS. 5–8, when using an armed trocar 20, initially tip 196 of safety shield 190 is placed into contact with the exterior skin 500 of a patient, typically a mammal, such that the longitudinal axis of trocar 20 is substantially perpendicular to the surface of the skin, although the axis can be angulated at acute or obtuse angles with respect to the skin surface (see FIG. 5). A forward or distal force is applied against the trocar obturator handle 180 typically causing the safety shield 190 to displace proximally against coil spring 205 thereby compressing spring 205 and exposing piercing tip 160 as piercing tip 160, along with safety shield 190 and cannula tube 80 are pushed through the exterior skin 500 and underlying fat, muscle and fascia 525 into the underlying body cavity 550 (see FIGS. 5, 6, 6A, and 7). When the trocar obturator 150 initially encounters resistance to penetration, it is typically displaced, proximally, against spring member 189 into cavity 188 of handle 180, thereby causing the actuating means to actuate the locking mechanism. Once the piercing tip 160 and bullet shaped tip 196 enter the body cavity 550, the distal biasing force applied by compressed spring 205 causes the safety shield 190 to rapidly slide distally, or snap, to an extended position, thereby covering piercing tip 160 as seen in FIG. 7. The safety shield 190 is locked in place by the lockout arm 230.

The safety shield locking mechanism operates in the following manner (see FIGS. 5, 6, 6A, 7 and 8). Prior to using the trocar 20, the surgeon arms the safety shield locking mechanism by displacing the reset button 270 in a distal, axial direction. Displacing reset button 270 distally causes the tab members to engage the back side of the lockout arm 230, reset tabs and cam the lockout arm forward causes the tab members 276 to engage the back side of the lockout arm reset tabs 235 and cam the lockout arm forward. This allows the knife collar 250 to move distally and hold the lockout arm 230 in the armed position (safety shield 190 is free to move proximally). Releasing the reset button 270, allows the members 276 of the reset button 270 to rest against the tabs 235 of the lockout arm 230. The reset button 270 is held in its distal position, indicating that the trocar 20 is armed and ready for use. As the trocar 20 is actuated, the safety shield 190 is free to slide proximally. In addition, knife collar arm 260 is no longer contained in knife collar clearance hole 234 as a result of the rotational displacement of lockout arm 230. This allows the obturator shaft 155 and knife collar 250 to displace distally such that the knife collar arm 260 is positioned whereby it engages the inner side of lockout arm 230. When armed, the distal end 240 of lockout arm 230 is maintained out of the way of the flange 198 of the safety shield 190 by the knife collar arm 260 which engages the lockout arm 230 and maintains it in an outwardly rotated position. When the armed trocar 20 is inserted into a body cavity by a surgeon, initially the safety shield 190 drives back proximally simultaneously with, or just before, proximal movement of obturator shaft 155. As the obturator shaft 155 and knife collar 250 displace proximally, the knife collar arm 260 moves off of the lockout arm 230 and into the knife collar clearance hole 234 allowing the lockout 230 arm to return to its free state. Movement of the lockout arm 230 to its free state, releases the reset button 270 and allows the reset button 270 to return to its proximal position. As the tab members 276 pass on the front side of the reset tabs 235, the tab members 276 cam the lockout arm 230 back. After the tab members 276 have passed the tabs 235, the lockout arm 230 returns to its free state. In this position, the lockout arm 230 is ready to be rearmed. When the distal end of the trocar obturator 170 enters the body cavity, the spring 205 snaps the safety shield 190 into a forward, distal extended position, and the locking arm 230 is free to rotate into the locking position (since knife collar arm 260 is now contained in clearance hole 234) wherein distal end 240 engages flange 198 thereby preventing the safety shield 190 from moving proximally. The optional knife collar arm 263 functions as a safety backup for engaging the safety shield locking mechanism. Specifically, in instances where distal displacement of shield 190 occurs prior to sufficient distal displacement of obturator 150 effective to actuate the locking mechanism, flange 198 will contact the distal end 264 of arm 263, thereby driving the collar 250 proximally such that arm 260 is displaced into clearance hole 234 and lockout arm 231 is free to rotate inwardly to contact flange 198 of shield 190.

In order to rearm the locking mechanism, the reset button 270 is again displaced distally, thereby causes the tab members 276 to engage the back side of the lockout arm reset tabs 235 and cam the lockout arm forward. This allows the knife collar 250 to move distally and hold the lockout arm 230 in the armed position (safety shield 190 is free to move proximally). Releasing the reset button 270, allows the members 276 of the reset button 270 to rest against the tabs 235 of the lockout arm 230. The reset button 270 is held in its distal position, indicating that the trocar 20 is armed and ready for use. The knife collar 250 is preferably bonded or mounted to the proximal end of the obturator shaft 155 so that it moves with the shaft 155.

The position of the reset button 270 indicates whether or not the trocar 20 is in an armed configuration. A trocar 20 is armed when the safety shield 190 is in an unlocked configuration. Specifically, when the trocar 20 is armed and safety shield 190 is unlocked, the reset button 270 will be in a distal position with respect to handle 180. When the trocar 20 is in an unarmed configuration, the reset button 270 will be in a proximal position with respect to handle 180.

Trocar obturator assembly 170 is removed from trocar cannula 30 by pivotally displacing the latches 220 inwardly into obturator handle 180, thereby releasing tab members 225 from cavities 327. Simultaneously, a proximal or pulling force is applied to the obturator handle 180 of trocar obturator assembly 170 causing the obturator shaft 155 and safety shield 190 to slide out of the trocar cannula 50. As the tip 196 enters tubular member passageway 77, the face 105 of flapper valve 100 is displaced against sealing ring 81 by spring 107 and seated, thereby sealing off the tubular member 77 and producing a gas-tight seal.

The trocars 20 of the present invention are made of conventional materials having the requisite biocompatibility and mechanical requirements. The trocar obturator 150 may be typically manufactured from conventional materials including polymers such as polycarbonate, metals such as stainless steel, ceramics, polyetherimide, and conventional biocompatible materials and equivalents thereof. The piercing tip 160 may be manufactured from conventional materials including biocompatible metals such as stainless steel, ceramics, plastics and the like. The trocar cannula 30 and the obturator handle 180 and safety shield 190 as well as the lockout arm 230 are preferably molded from conventional materials including biocompatible polymers such as polycarbonate, polyether-imide, silicone rubbers and the like. The molded components are molded using conventional molding equipment utilizing conventional processes.

Trocars are conventionally used to provide access to a surgical site in a patient's body cavity. A trocar 20 is typically inserted by pressing the distal end of the trocar 20 against the outer skin 500 of the patient (see FIGS. 5, 6, 6A, and 7). The insertion site is selected by the surgeon to provide optimal access to the target surgical site within the body cavity 550. Sufficient force is applied to the trocar obturator handle 180 in a direction along the longitudinal axis of the trocar so that the piercing tip 160 of the trocar obturator 155 effectively penetrates the patient's skin, underlying fat tissue, muscle and fascia 525. The distal end of the trocar 20 is then located by the surgeon to a position effective for access to the target surgical site. Then the trocar obturator assembly 170 is removed from the trocar cannula 30 by applying a rearward force to the trocar obturator handle 180. The trocar cannula 30 is then used as a passageway to and from the patient's body cavity 550.

The endoscopic surgical method of the present invention uses the trocars of the present invention, such as trocar 20, having trocar cannulas 30 and trocar obturator assemblies 170. The surgical method initially involves the preparation of the patient for endoscopic surgery, in a conventional manner, e.g., inducing a pneumoperitoneum, and insertion of at least one trocar 20 of the present invention into a body cavity of the patient, using conventional endoscopic surgical techniques. Endoscopic surgical techniques are disclosed in the *Textbook Of Laparoscopy*, Jaroslav F. Hulka, M.D., Grune and Stratton, Inc., New York (1985), and in *Laparoscopy For Surgeons*, Barry A. Salky, M.D., IGAKU-SHOIN Medical Publishers, New York (1990), which are incorporated by reference. The trocar assembly 170 is then removed from the cannula 30 and the trocar cannula 30 is available as a passageway to and from the body cavity. When using a trocar cannula in an endoscopic procedure, such as trocar cannula 30, the trocar cannula handle 55 is typically disposed exterior to the body cavity wall while the distal end 85 of the cannula tube 80 is within the body cavity. Various conventional endoscopic surgical instruments, surgical staplers, sutures, needles, pharmaceuticals, tissue, tissue samples, drug delivery devices, electrosurgical devices, electrodes, etc., are inserted through the trocar cannula 30 and maneuvered to the target surgical site where conventional endoscopic surgical techniques are utilized.

The following examples are illustrative of the principles and practice of the present invention.

EXAMPLE 1

A patient of conventional size and weight was prepared for surgery using conventional techniques including depilation of the epidermis in the region of expected incision, scrubbing and rinsing with conventional fluids, and application of a conventional iodine solution. The patient was placed in a reclining position on a conventional operating table and covered with a sterile drape. The patient was anesthetized with a sufficient dose of a conventional anesthetic effective to induce an anesthetized state.

The patient was cannulated with an endotracheal tube and connected to a conventional anesthesia machine and ventilated as required. The abdominal cavity of the patient was insufflated in a conventional manner with carbon dioxide and five trocars 20 of the present invention were inserted into the abdominal cavity. Each trocar 20 was armed prior to insertion by displacing reset button 270 distally. The insertion site was pierced with a scalpel. Upon pressing the piercing tip 160 of each trocar 20 against the exterior of the abdominal wall, a skin incision was initiated as the obturator shaft 155 first moved proximally with respect to trocar 20, thereby actuating the locking mechanism for the safety shield 190, and then moved distally with trocar 20 toward and into the body cavity. Upon entry into the body cavity, the safety shield 190 of each trocar was snapped forward to an extended position by spring 205. The safety shields 190 were locked in an extended position covering the piercing tip 160 of each trocar 20 thereby preventing inadvertent piercing of internal organs, tissue or blood vessels. Then, the obturator assemblies 170 were removed so that the trocar cannulas 30 remained in the abdominal cavity as pathways. An endoscope was inserted through one of the trocar cannulas 30. The endoscope was connected to a video monitor.

EXAMPLE 2

A human patient is prepared for surgery using conventional preparatory techniques and is effectively anesthetized using a sufficient dose of a conventional anesthetic. The patient is connected to conventional anesthesiology equipment, and as needed, ventilation equipment. After using conventional endoscopic preparatory procedures, including insufflation and insertion of an endoscope, three trocars 20 of the present invention are inserted into the abdominal cavity of the patient by pressing the distal end of each trocar 20 into the exterior skin 500 of the patient in the proximity of the target surgical site (see FIGS. 5, 6, 6A, 7 and 8). Prior to insertion the trocars 20 are armed by displacing each reset button 270 distally. Sufficient force is exerted by the surgeon on the trocar obturator handle 180 effective to cause the piercing tip 160 of the trocar obturator assembly 170 to pierce through the patient's skin (optionally the surgeon cuts with a scalpel) and underlying fat, muscle tissue, and fascia (along with safety shield 190). Then, the end of the trocar is brought into a position in the body cavity which is in the proximity of the target surgical site. Rearward or proximal movement of the obturator shaft 155 actuates the safety shield locking mechanism as the piercing point 160 pierces the skin and underlying layers of tissue 525. After entry into the body cavity 550, the safety shield 190 is displaced distally by the bias of spring 205 to an extended position covering piercing tip 160 and is locked in place by the safety shield locking mechanism. The trocar obturator assembly 170 is then removed from the trocar cannula 30 and the safety shield 190 remains in a locked, extended position covering piercing tip 160. An incision is made in the target site using a conventional endoscopic cutting instrument inserted through a cannula 30 and a piece of tissue is removed by grasping the tissue with a conventional endoscopic grasper and extracting the tissue through another trocar cannula 30. The trocar cannula 30 is made from a transparent material thereby enabling the surgeon to observe the tissue as it is guided through and out of the cannula 30.

The surgeon then inserts an endoscopic surgical needle and suture, using a conventional endoscopic needle holder, through a trocar cannula 30. The surgeon sutures the incision at the target surgical site, using conventional endoscopic surgical techniques, and removes the surgical needle and excess suture through the trocar cannula 30.

Next the trocar cannulas 30 are removed from the patient. Finally, the trocar insertion sites are closed by conventional taping, suturing, and/or stapling techniques.

There are many advantages of the trocar locking mechanism of the present invention and the trocars 20 containing the locking mechanism. The rearming of the safety shield locking mechanism can be accomplished with one hand. That is, the surgeon while holding trocar 20 with one hand can arm the trocar by sliding reset button 270 with a thumb or other finger on that hand. In addition, the re-set button 270 of the trocar obturator of the present invention provides a visual indication of the status of the lockout mode as to whether it is armed or unarmed. That is, button 270 is distal when in an armed mode and proximal when unarmed with safety shield 190 locked. A further advantage of the trocars 20 is that the lockout mechanism works off of the movement of the obturator and may be more sensitive than a safety mechanism actuated solely by safety shield movement.

Although this invention has been shown and described with respect to detailed embodiments thereof, it will be understood by those skilled in the art that various changes in form and detail thereof may be made without departing from the spirit and scope of the claimed invention.

What is claimed is:

1. A trocar obturator assembly, comprising:
   a hollow obturator handle;
   an elongated obturator shaft having a proximal end and a distal end, the proximal end of the obturator shaft slidably mounted in the handle;
   a piercing tip mounted to the distal end of the obturator shaft;
   a safety shield slidably mounted on the obturator shaft, said safety shield concentrically disposed about the obturator shaft, and moveable to an extended position and a retracted position, said safety shield comprising an elongated tube member having a proximal end and distal end and said safety shield further comprising a flange mounted to the proximal end;
   biasing means mounted in the handle and acting upon the flange of the safety shield for moving the safety shield to an extended position;
   locking means mounted in the handle for locking the safety shield in an extended position; and,
   actuating means mounted in the handle for locking the safety shield in an extended position; and,
   actuating means mounted in the handle for actuating the locking means in response to axial, proximal motion of the obturator shaft.

2. The trocar obturator of claim 1 further comprising means for resetting the locking means so that the safety shield is free to slide proximally, said resetting means mounted in the trocar obturator handle.

3. The trocar obturator of claim 1 wherein the locking means comprises a lockout arm having a proximal fixed end mounted in the handle and a distal free end for engaging the safety shield flange such that in a locked position, the distal free end of the lockout arm engages the safety shield flange thereby locking the safety in a distal, extended position.

4. The trocar obturator assembly of claim 2 wherein the locking means comprises a lockout arm having a proximal fixed end mounted in the handle and a distal free end for engaging the safety shield flange such that in a locked position, the distal free end of the lockout arm engages the safety shield flange thereby locking the safety in a distal, extended position.

5. The trocar obturator assembly of claim 4 wherein the resetting means comprises a button means slidably mounted in the obturator handle, said button means engaging the lockout arm such that the lockout arm rotates about its fixed end in response to sliding motion of the button means.

6. The lockout arm of claim 3 further comprising a hole therethrough.

7. The trocar obturator assembly of claim 1 wherein the actuating means comprises collar means mounted to the proximal end of the obturator shaft and contained within the obturator handle and moveable with the obturator shaft such that proximal movement of the obturator shaft results in proximal movement of the collar means, thereby causing engagement of the locking means to lock the safety shield in an extended position.

8. The collar means of claim 7 comprising:
   an annular member having an axial hole therethrough and having an outer circumferential periphery;
   a mounting member radially extending from the periphery; and,
   a collar arm extending axially from the mounting member.

9. The trocar obturator assembly of claim 1 wherein the distal biasing means for the safety shield comprises a spring having a proximal end and a distal end, said spring concentrically mounted in the obturator handle about the proximal end of the obturator shaft such that the proximal end of the spring contacts a retaining ring means mounted to the shaft and the distal end of the spring is in contact with the safety shield flange.

10. The trocar obturator assembly of claim 1 further comprising biasing means mounted in the obturator handle for biasing the obturator shaft distally, axially.

11. The collar means of claim 8 further comprising a second radially extending mounting member and a second axially extending collar arm.

12. A trocar, comprising:
   A. a trocar obturator assembly, comprising
   a hollow obturator handle;
   an elongated obturator shaft having a proximal end and a distal end, the proximal end of the obturator shaft slidably mounted in the handle;
   a piercing tip mounted to the distal end of the obturator shaft;
   a safety shield slidably mounted on the obturator shaft, said safety shield concentrically disposed about the obturator shaft, and moveable to an extended position and a retracted position, said safety shield comprising an elongated tube member having a proximal end and distal end and said safety shield further comprising a flange mounted to the proximal end;

biasing means mounted in the handle and acting upon the flange of the safety shield for moving the safety shield to an extended position;

locking means mounted in the handle for locking the safety shield in an extended position; and, actuating means mounted in the handle for actuating the locking means in response to axial, proximal motion of the obturator shaft, and a trocar cannula having an interior passage therethrough for receiving the trocar obturator assembly, said cannula comprising an elongated trocar cannula tube and a trocar cannula handle for mounting said cannula tube.

13. The trocar obturator of claim 12 further comprising means for resetting the locking means so that the safety shield is free to slide proximally, said resetting means mounted in the trocar obturator handle.

14. The trocar obturator of claim 12 wherein the locking means comprises a lockout arm having a proximal fixed end mounted in the handle and a distal free end for engaging the safety shield flange such that in a locked position the distal free end of the lockout arm engages the safety shield flange such that the safety shield is locked in a distal, extended position.

15. The trocar obturator of claim 13 wherein the locking means comprises a lockout arm having a proximal fixed end mounted in the handle and a distal free end for engaging the safety shield flange such that in a locked position, the distal free end of the lockout arm engages the safety shield flange thereby locking the safety shield in a distal, extended position.

16. The trocar obturator of claim 15 wherein the resetting means comprises a button means slidably mounted in the obturator handle, said button means engaging the lockout arm such that the lockout arm rotates about its fixed end in response to sliding motion of the button means.

17. The lockout arm of claim 14 further comprising a hole therethrough.

18. The trocar of claim 12 wherein the actuating means comprises collar means mounted to the proximal end of the obturator shaft and contained within the obturator handle and moveable with the obturator shaft such that proximal movement of the obturator shaft results in proximal movement of the collar means, thereby causing engagement of the locking means to lock the safety shield in the extended position when pressure is released from the safety shield.

19. The collar means of claim 18 comprising:
an annular member having an axial hole therethrough and having an outer circumferential periphery;
a mounting member radially extending from the periphery; and,
a collar arm extending axially from the mounting member.

20. The trocar obturator assembly of claim 12 wherein the distal biasing means for the safety shield comprises a compression spring having a proximal end and a distal end, said spring concentrically mounted in the obturator handle about the proximal end of the obturator shaft such that the proximal end of the spring contacts a retaining ring means mounted to the shaft and the distal end of the spring is in contact with the safety shield flange.

21. The trocar obturator assembly of claim 12 further comprising biasing means mounted in the obturator handle for biasing the obturator shaft distally, axially.

22. The collar means of claim 19 further comprising a second radially extending mounting member and a second axially extending collar arm.

23. The trocar obturator assembly of claims 1 or 12 further comprising means for actuating the locking means in response to proximal motion of the safety shield.

24. A method of performing an endoscopic surgical procedure, comprising
I. inserting a trocar into a body cavity, wherein the trocar comprises
A. a trocar obturator assembly, comprising a hollow obturator handle;
an elongated obturator shaft having a proximal end and a distal end, the proximal end of the obturator shaft slidably mounted in the handle;
a piercing tip mounted to the distal end of the obturator shaft;
a safety shield slidably mounted on the obturator shaft, said safety shield concentrically disposed about the obturator shaft, and moveable to an extended position and a retracted position, said safety shield comprising an elongated tube member having a proximal end and a distal end and said safety shield further comprising a flange mounted to the proximal end;
biasing means mounted in the handle and acting upon the flange of the safety shield for moving the safety shield to an extended position;
biasing means mounted in the handle for biasing the obturator in a distal direction;
locking means mounted in the handle for locking the safety shield in an extended position; and,
actuating means mounted in the handle for actuating the locking means in response to axial, proximal motion of the obturator shaft, and
B. a trocar cannula having an interior passage therethrough for receiving the trocar obturator assembly, said cannula comprising an elongated trocar cannula tube and a trocar cannula handle for mounting said cannula tube;
II. removing the trocar obturator assembly from the trocar cannula; and,
III. using the cannula as a pathway to and from the body cavity.

* * * * *